United States Patent [19]

Mobley et al.

[11] Patent Number: 5,049,496

[45] Date of Patent: Sep. 17, 1991

[54] METHOD FOR MICROBIOLOGICALLY HYDROXYLATING BIPHENYL AND TERPHENYL COMPOUNDS

[75] Inventors: David P. Mobley; David K. Dietrich, both of Schenectady, N.Y.

[73] Assignee: General Electric Company, Schenectady, N.Y.

[21] Appl. No.: 632,887

[22] Filed: Dec. 24, 1990

[51] Int. Cl.[5] .................. C12P 15/00; C12P 13/00; C12P 11/00; C12R 1/66

[52] U.S. Cl. ........................ 435/127; 435/128; 435/130; 435/135; 435/147; 435/156; 435/254; 435/913

[58] Field of Search ............ 435/127, 128, 130, 135, 435/147, 156, 913, 254

[56] References Cited

U.S. PATENT DOCUMENTS 4,431,736  2/1984  Romesser ..................... 435/156
4,981,793  1/1991  Johnson et al. ................ 435/156

OTHER PUBLICATIONS

Salvo et al., *Biotechnol. Prog.*, 6, 193–197 (1990).
Cox et al., Biotechnol. Bioeng., 1985, 27, 1395–1402.

*Primary Examiner*—Herbert J. Lilling
*Attorney, Agent, or Firm*—William H. Pittman; James C. Davis, Jr.

[57] ABSTRACT

*A. parasiticus* is employed to hydroxylate biphenyls or terphenyls. The hydroxylation reaction is enhanced by gradually adding a carbon source to the culture medium-reaction medium, preferably in an amount to maintain the ammonium level below 300 ppm. during the bioconversion phase. Employment of a mutant strain of *A. parasiticus* which was isolated following ultraviolet light mutagenesis to reduce its tendency to produce aflatoxins is preferred.

8 Claims, No Drawings

METHOD FOR MICROBIOLOGICALLY HYDROXYLATING BIPHENYL AND TERPHENYL COMPOUNDS

This invention relates to the microbiological oxidation of biphenyls and terphenyls, employing a strain of *Aspergillus parasiticus* (*A. parasiticus*). More particularly, the invention concerns the slow addition of a carbon source to the culture medium-reaction medium containing such *A. parasiticus* and a biphenyl or terphenyl.

Microbiological oxidation of biphenyls by a variety of bacteria and fungi including *A. parasiticus* has been studied. For a discussion of the background of the art see U.S. Pat. Nos. 4,153,509 and 4,431,736, which patents are hereby incorporated by reference, and the references cited therein. *Chemical Abstracts* has a reference to a compound which could be confused with a hydroxylated terphenyl as being disclosed in *J. Chromatogr. Libr.*, 30, 35-44 (1985), but the Chemical Abstracts reference is clearly in error since the publication referred to is directed to phenolformaldehyde condensation products.

Hydroxylated aromatic molecules have commanded considerable interest in industry due to their many uses in the manufacture of plastics, liquid crystals and dyes. However, some large-scale selective hydroxylations are difficult to carry out by any means.

Often, relatively inexpensive starting materials can be biologically converted to higher value products. One organism capable of performing an interesting bioconversion is *A. parasiticus*. It has been reported that this fungus can transform biphenyl to 4,4'-dihydroxybiphenyl in batch and continuous cultures but the reported rates and concentrations were judged to be too low to be economically attractive. It has now been discovered that final product concentrations can be increased by slow addition of a carbon source to the culture medium-reaction medium used to oxidize aromatic compounds to the corresponding hydroxylated derivatives.

Accordingly, the present invention is a method for preparing a hydroxylated biphenyl or terphenyl which comprises microbiologically oxidizing a compound selected from the group consisting of biphenyls and terphenyls by the action of *Aspergillus parasiticus,* and simultaneously adding a carbon source.

The present invention is applicable to the hydroxylation of all biphenyl and terphenyl compounds having a free hydroxylation site. Such compounds may be represented by the formula

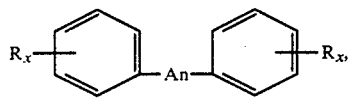

(I)

wherein each R is a substituent inert to bioconversion conditions (e.g., alkyl, halo, hydroxy or carboxy), A is a divalent radical, x has a value from 0 to 4 and n is 0 or 1. The divalent radicals represented by A include saturated and unsaturated, cyclic and acyclic, divalent hydrocarbon radicals which may be substituted with R radicals, divalent amino such as aromatic or aliphatic amino, azo, divalent carbonyloxy, carbonyl, ether and thio radicals. Most often, A is alkylene, alkenylene or m-phenylene, including 2'-hydroxy-m-phenylene. Compounds having no A radical (i.e., those in which n is 0) are also contemplated.

Among the compounds which can be hydroxylated by the process of this invention are the 2'-hydroxy-m-terphenyls, which produce m-terphenyltriols. Said 2'-hydroxy-m-terphenyls are represented by the generic formula

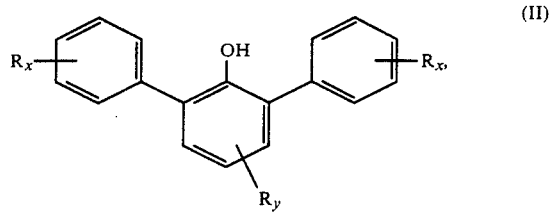

(II)

wherein y has a value from 0 to 3. Any free position of any ring radical of the 2'-hydroxy-m-terphenyl, except the 4 and 4" position, may contain an R radical.

Preferred R values are alkyl, alkylamino and alkoxy radicals, especially $C_{1-4}$ alkyl. Preferably, each x and each y is independently 0-2.

The m-terphenyltriols include 2', 4,4"-m-terphenyltriols having the formula

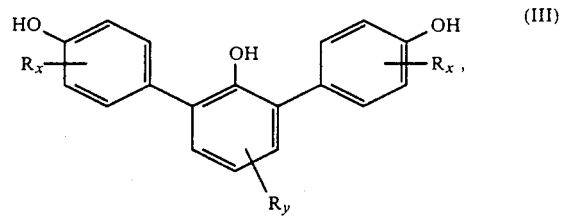

(III)

in which R, x and y are as previously defined. A preferred m-terphenyltriol has the formula

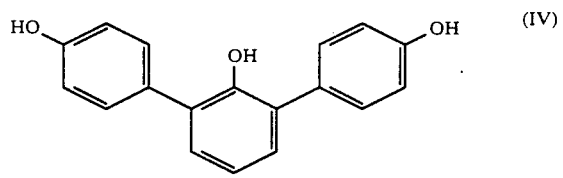

(IV)

These 2',4,4"-m-terphenyltriols and the method for their preparation are disclosed and claimed in copending, commonly owned application Ser. No. 07/632,888. They may be prepared by microbiological oxidation of a corresponding 2'-hydroxy-m-terphenyl by the action of *A. parasiticus.* Preferably, a strain of *A. parasiticus* which has decreased tendency to produce aflatoxins is employed.

The medium in which the *A. parasiticus* is preferably cultivated includes a carbon source, a nitrogen source and deionized water. Suitable carbon sources include glucose, maltose and fructose, with glucose generally being preferred. Readily available forms of glucose such as corn syrup are particularly useful.

As nitrogen sources, such commonly employed materials as ammonium salts, corn steep liquor, peptone, neopeptone, soytone, tryptone and soybean powder may be employed. Corn steep liquor is particularly suitable and is generally preferred.

The culture medium can also contain various trace elements. These are generally conventional in nature, and include boron, copper, zinc, magnesium, iron, manganese and cobalt. They may be furnished in the form of readily available compounds.

The usual method of growing *A. parasiticus* involves a rich medium containing both carbon and nitrogen sources, in which the fungal spores are germinated and grown for about 24 hours. The resulting culture is used to inoculate a larger batch of medium, also for about 24 hours. At the end of this time, near-maximum cell density has been achieved and the available carbon and nitrogen are nearly depleted. This portion of the biochemical process is sometimes hereinafter designated the "growth phase". The compound to be hydroxylated, in the present case the 2'-hydroxy-m-terphenyl, is then added and undergoes oxidation in what is hereinafter termed the "bioconversion phase".

It has been discovered that when all the carbon source and nitrogen source are introduced at the beginning of the growth phase, the ammonium ion concentration of the system increases during the bioconversion phase from a value near zero at the beginning thereof. Concurrently, the pH of the system increases. When the ammonium ion concentration exceeds about 300 ppm., the conversion of biphenyls/triphenyls to hydroxylated derivatives ceases.

According to the present invention, therefore, carbon source is added gradually during said phase. One effect of such gradual addition is to maintain the ammonium ion concentration at a low level. The rate of pH increase is concomitantly retarded.

It is believed that the effect of gradual addition of carbon source during the bioconversion stage is based on the property of *A. parasiticus* to undergo different metabolic processes in various life stages. Thus, the method of this invention keeps the organism in the metabolic state in which the desired bioconversion takes place, while an increase in ammonium ion concentration is a signal that the organism is leaving this metabolic state. The concentration of ammonium ion in the system can be used as an index of the proper rate of addition of the carbon source. If the rate of addition is too high, the bioconversion stops, most likely because of catabolite repression.

Thus, it is well within the state of the art to regulate the addition rate of the carbon source to obtain optimum results. Both constant and variable addition rates may be employed. Suitable addition rates are often in the range of about 0.001-1.0, preferably about 0.05-0.5 and most preferably about 0.1 gram/liter/hour.

The pH of the culture medium may vary from about 3.5 to about 9 and preferably from about 5.5 to about 7. It is often convenient to buffer the pH in this range by employing as a nitrogen source corn steep liquor or a peptone, which contain buffering amino acids, or by acid or base addition. Cultivation temperatures of the *A. parasiticus* are typically in the range of about 20°-40° C. and preferably about 30°-37° C.

The biphenyl or terphenyl to be oxidized may be introduced into the culture medium neat (i.e., in the absence of solvent) or in a suitable solvent which is non-toxic to the microorganism. Methanol and ethanol are illustrative of such solvents.

In a preferred embodiment of this invention, the substrate is added as a fine aqueous dispersion, allowing for the addition of large amounts of substrate with maximum available surface area for interaction with the microorganism and further avoiding the inhibition of microorganism growth and activity which may occur with even low concentrations of organic solvents. Such dispersions can be easily prepared; for example, by high-shear stirring of the molten substrate at temperature above the melting point thereof with gelatin as an emulsifying agent, followed by cooling to ambient temperature with continued stirring. Using such a technique, substrate particle size can be reduced to less than 10 microns.

Additionally, as an alternative to preparing a fine dispersion of the substrate, such substrate can be admixed or dispersed in a surfactant before addition to the culture medium. Generally such surfactants are useful in amounts in the range of about 0.1-0.6% by weight of the culture medium-reaction mixture.

Examples of suitable surfactants include polyoxyethylene octylphenyl ether, available as Noniodet P40, Triton X-100 and Igepal CA. The formula of these materials is 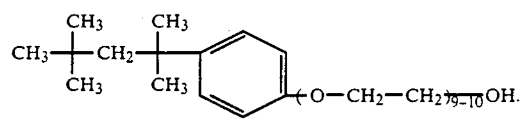 Additional examples of surfactants are polyoxyethylene (20) acetyl ether and polyoxyethylene (4) lauryl ether, available as Brij, 58 and 30, respectively; polyoxyethylene nonylphenyl ether, available as Igepal CO; and polyoxyethylene (20) sorbitan monolaurate, polyoxyethylene (20) monooleate and polyoxyethylene (20) sorbitan monopalmitate, available as Tweens, 20, 80 and 40, respectively. The presence of such surfactants in the culture medium containing microorganism and the reactant/substrate is believed to maximize microorganism-substrate contact by enhancing solubility of the sparsely water-soluble substrate. The presence of a surfactant has been found to substantially increase product concentration.

The concentration of the *A. parasiticus* required according to this invention is typically about 1-2% by weight (dry), particularly in the case of *A. parasiticus* grown on corn steep liquor.

The invention is illustrated by the following examples. All parts and percentages are by weight unless otherwise specified.

EXAMPLE 1

Spores of *A. parasiticus* strain ATCC 15517 were plated on Sabouraud Dextrose (Difco) with Bacto agar added to 1.5%, and irradiated with a germicidal UV light source at 60 microwatt hours per square centimeter measured at the culture plate surface. Approximately 99% of the irradiated spores failed to germinate. Spores that did germinate were transferred to aflatoxin production plates as described by Lennox and Davis, "Selection of and Complementation Analysis Among Aflatoxin Deficient Mutant of *Aspergillus parasiticus*", *Exp. Myco.*, 8, 192-195 (1983), which description is hereby incorporated by reference. Four colonies were inoculated per plate with a wild-type control at the center. Decreased aflatoxin producers were screened by illuminating the plates with a long-wave UV lamp (366 nm.) and by looking for the absence of a blue halo, which normally surrounds a wild-type colony. Several low-level aflatoxin producers were isolated after screening several thousand colonies that developed from UV-irradiated spores.

Thin layer chromatography and high pressure liquid chromatography were used to detect aflatoxins after extraction from spent media, mycelia or agar plates. Aflatoxin standards (Sigma) were always run in parallel. These analyses showed that strain JS 1-89 produced no detectable aflatoxins. The hydroxylation activity of strain JS 1-89 was comparable to wild type isolates.

The spore production agar was prepared by dissolving in water 218 g. of sorbitol, 5 g. of yeast extract, 20 ml. of Aspergillus minimal salts solution, 1 ml. of trace elements solution, 10 g. of glucose and 15 g. of Bacto-Agar, autoclaving the solution and combining it with 10 ml. of 0.2M magnesium sulfate heptahydrate solution. The Aspergillus minimal salts solution was prepared by dissolving in 1 liter of water 300 g. of sodium nitrate, 75 g. of potassium dihydrogen phosphate and 25 g. of potassium chloride and adjusting the pH to 6.5 by addition of sodium hydroxide. The trace elements solution was prepared by dissolving in 1 liter of water 500 mg. of boric acid, 40 mg. of cupric sulfate pentahydrate, 100 mg. of potassium iodide, 200 mg. of ferric chloride monohydrate, 160 mg. of molybdic acid and 400 mg. of zinc sulfate heptahydrate. The spore harvesting buffer was an aqueous solution of 1% sodium chloride, 0.1% Triton X-100 surfactant and 20% glycerol.

A stock of spores of strain JS 1-89 was prepared by inoculating spore production agar with $5 \times 10^5$ spores of the strain and incubating for two days at 30° C., then at room temperature until a heavy "lawn" of green spores had developed. They were suspended in spore harvesting buffer, spun down, resuspended in fresh buffer, diluted to the desired concentration and stored at $-80°$ C. An inoculum culture was prepared by charging five 2-liter baffled Erlenmeyer flasks with 400 ml. of sterile Sabouraud Dextrose, inoculating with JS 1-89 spores at $6 \times 10^8$ spores per flask and incubating for 24 hours at 37° C.

A 400-liter straight-sided polyethylene tank fitted with a motor-driven stirrer was chemically sterilized with sodium hypochlorite and isopropyl alcohol, charged with 300 liters of an aqueous solution comprising 22 g./l. Karo corn syrup, 43 g./l. Argo Steepwater E801 corn steep liquor and 20 mg./l. tetracycline hydrochloride as a bacterial suppressor, inoculated with the contents of the spore germination flasks, and sparged with sterilized air at 37° C. for 24 hours.

There were then added, with stirring, 600 grams of 2'-hydroxy-m-terphenyl, 1200 grams of Triton X-100 surfactant and 15 grams of 4,4'-biphenol as a promoter. Air sparging was continued as an aqueous solution containing 300 g./l. of corn syrup was added at 0.05 g./l./hr. of corn syrup for the first 65 hours, 0.12 g./l./hr. for the next 95 hours and 0.008 g./l./hr. until bioconversion was complete. The pH and ammonium ion concentration of the mixture were monitored during the bioconversion.

When bioconversion was complete, the mixture was brought to a pH of 12 and the contents were centrifuged. The solids were reslurried at pH 12 and recentrifuged and the combined liquid phases were acidified to a pH of 7 and extracted with ethyl acetate. The extracts were purified by liquid/liquid extraction and flash chromatography to yield 102 grams of 2', 4,4''-m-terphenyltriol. The structure of the product was confirmed by proton and carbon-13 nuclear magnetic resonance and mass spectrometry and it was shown by high pressure liquid chromatography and gas chromatography to be greater than 99% pure.

EXAMPLE 2

The procedure of Example 1 was repeated up to and including the microorganism growth in the polyethylene tank. Separate dispersions of m-terphenyl and 4,4'-biphenol were prepared by autoclaving 20 grams of each compound in admixture with 2 grams of gelatin and 80 ml. of water, blending in a high-shear mixer and cooling.

To the tank were added m-terphenyl dispersion in the amount of 1 gram of m-terphenyl, together with 5 grams of Triton X-100 surfactant, to respective concentrations of 1 and 5 grams per liter, followed by 4,4'-biphenol dispersion to a concentration of 50 mg. per liter. Additional m-terphenyl dispersion was introduced as needed. Corn syrup was also added as in Example 1 but at a rate of 0.12 g./l./hr.

When bioconversion was complete, the mixture was brought to a pH of 12 by addition of aqueous sodium hydroxide and the mycelial mass was removed by centrifugation, reslurried in aqueous base and again centrifuged. The combined aqueous solutions were brought to a pH of 14 and extracted with methylene chloride followed by ethyl acetate. The ethyl acetate extracts were stripped, dissolved in 1M aqueous sodium hydroxide and again extracted with methylene chloride followed by ethyl acetate, and the ethyl acetate was again stripped. The residue was dissolved in acetone and further purified by flash column chromatography using a hexane/ethyl acetate mixture. There was obtained 136 grams of the desired 4'-4''m-terphenyldiol, isolated in 99% purity as shown by high pressure liquid chromatography.

EXAMPLE 3

The procedure of Example 1 was repeated up to and including the microorganism growth in the polyethylene tank. There was then added a molten aqueous mixture of 610 grams of methyl 4-biphenylcarboxylate, 1200 grams of Triton X-100 surfactant and 15 grams of 4,4'-biphenol, to produce a methyl 4-biphenylcarboxylate concentration of 2 grams per liter.

The mixture was sparged with air at 80 SLPM and 37° C. as corn syrup was added as in Example 1, but at rates of 0.07 g./l./hr. for the first 14 hours, 0.007 g./l./hr. for the next 32 hours and 0.1 g./l./hr. until bioconversion was complete. Aqueous sodium hydroxide solution was then added to bring the mixture to a pH of 11 and the mixture was centrifuged. The centrifugate was acidified to a pH of 3 and allowed to settle overnight, whereupon a nearly clear upper phase and a cloudy lower phase formed.

The lower phase was separated and centrifuged, and the solids were extracted with acetone and hot methanol. The combined extracts were stripped to yield 380 grams of the desired 4-hydroxy-4'-biphenylcarboxylic acid, shown by high pressure liquid chromatography to be 90% pure.

What is claimed is:

1. A method for preparing a hydroxylated biphenyl or terphenyl which comprises microbiologically oxidizing by the action of Aspergillus parasiticus a biphenyl or terphenyl having the formula

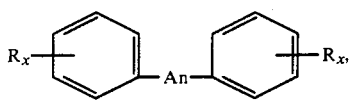 (I)

wherein each R is a substituent inert to bioconversion conditions, A is a divalent radical, x has a value from 0 to 4 and n i 0 or 1, and simultaneously adding a carbon source selected from the group consisting of glucose, maltose and fructose at a rate sufficient to maintain an ammonium level in the culture medium-reaction medium below about 300 ppm.

2. A method according to claim 1 wherein the strain of Aspergillus parasiticus employed is the ATCC 15517 strain.

3. A method according to claim 1 wherein a nonionic detergent is present in the amount of about 0.1–0.6 by weight of the reaction mixture.

4. A method according to claim 3 wherein the carbon source is added at a rate of about 0.001–1.0 gram per liter per hour.

5. A method according to claim 4 wherein the carbon source is added at a rate of about 0.05–0.5 gram per liter per hour.

6. A method according to claim 1 wherein the compound being hydroxylated is m-terphenyl.

7. A method according to claim 1 wherein the compound being hydroxylated is 2'-hydroxy-m-terphenyl.

8. A method according to claim 1 wherein the compound being hydroxylated is methyl 4-biphenylcarboxylate.

* * * * *